United States Patent
Sianawati

(10) Patent No.: US 9,642,367 B2
(45) Date of Patent: May 9, 2017

(54) MICROBICIDAL COMPOSITION

(71) Applicant: Dow Global Technologies LLC, Midland, MI (US)

(72) Inventor: Emerentiana Sianawati, Collegeville, PA (US)

(73) Assignee: DOW GLOBAL TECHNOLOGIE SLLC, Midland, MI (US)

( * ) Notice: Subject to any disclaimer, the term of this patent is extended or adjusted under 35 U.S.C. 154(b) by 0 days.

(21) Appl. No.: 15/108,485

(22) PCT Filed: Dec. 10, 2014

(86) PCT No.: PCT/US2014/069523
§ 371 (c)(1),
(2) Date: Jun. 27, 2016

(87) PCT Pub. No.: WO2015/102833
PCT Pub. Date: Jul. 9, 2015

(65) Prior Publication Data
US 2016/0316756 A1 Nov. 3, 2016

Related U.S. Application Data

(60) Provisional application No. 61/921,612, filed on Dec. 30, 2013.

(51) Int. Cl.
A01N 43/80 (2006.01)
A61K 8/49 (2006.01)
A61K 8/36 (2006.01)
A61Q 19/00 (2006.01)
D06M 16/00 (2006.01)
A01N 37/02 (2006.01)
A01N 37/04 (2006.01)
A01N 37/06 (2006.01)
A61L 2/232 (2006.01)

(52) U.S. Cl.
CPC ............. *A01N 43/80* (2013.01); *A01N 37/02* (2013.01); *A01N 37/04* (2013.01); *A01N 37/06* (2013.01); *A61K 8/361* (2013.01); *A61K 8/49* (2013.01); *A61Q 19/00* (2013.01); *D06M 16/00* (2013.01); *A61K 2800/10* (2013.01); *A61K 2800/524* (2013.01); *A61L 2/232* (2013.01)

(58) Field of Classification Search
CPC ........ A01N 43/80; A01N 37/04; A01N 37/06; A01N 37/02
See application file for complete search history.

(56) References Cited

U.S. PATENT DOCUMENTS

2007/0078118 A1 4/2007 Levy et al.
2009/0023688 A1 1/2009 Levy et al.
2009/0163445 A1 6/2009 Diehl et al.

FOREIGN PATENT DOCUMENTS

EP 2570502 A1 3/2013
FR EP 1772055 A1 * 4/2007 ............. A01N 43/80

OTHER PUBLICATIONS

Sieber et al (Skin Pharmacology and Physiology, 2014, 27(suppl 1): 9-17).*
Leeming et al (British Journal of Dermatology, 1986, 115, 551-556).*
Alakomi et al (Applied and Environmental Microbiology, May 2000, vol. 66, No. 5, pp. 2001-2005).*
McLain et al (Antimicrobial Agents and Chemotherapy, Oct. 2000, vol. 44, No. 10, pp. 2873-2875).*

* cited by examiner

Primary Examiner — Sudhakar Katakam
(74) Attorney, Agent, or Firm — Tifani M. Edwards

(57) ABSTRACT

Synergistic microbicidal compositions containing N-methyl-1,2-benzisothiazolin-3-one and natural organic acids.

3 Claims, No Drawings

MICROBICIDAL COMPOSITION

This invention relates to a synergistic combination of a selected microbicides having greater activity than would be observed for the individual microbicide.

MBIT is a new biocide chemistry which effectively preserves various water based products from microbial spoilage. However, sometimes a single active compound cannot provide an effective overall control of microorganisms due to efficacy gaps against certain microorganism types or the requirement of high use concentrations which prevent the chemistry from becoming a commercially viable product due to cost to treat barriers. For example, U.S. Pat. App. Pub. No. 2007/0078118 discloses synergistic combinations of N-methyl-1,2-benzisothiazolin-3-one (MBIT) with other biocides. However, there is a need for additional combinations of microbicides having enhanced activity against various strains of microorganisms to provide effective control of the microorganisms. Moreover, there is a need for combinations containing lower levels of individual microbicides for environmental and economic benefit. Currently markets like the home and personal care market are looking for products based upon natural ingredients. While MBIT is an ingredient often used in the home and personal care market it would be advantageous to be able to minimize the amount of MBIT used and combine it with a natural ingredient, while maintaining the same or better effectiveness.

The problem addressed by this invention is to provide such additional combinations of microbicides. Combinations of different antimicrobial compounds or other ingredients in the formulation, especially if they are synergistic, can broaden activity against various microorganisms, lessen overall biocide usage, aid in the minimization of environmental footprint and also expand potential market applications. This invention addresses the potential problems mentioned above and provides insight to MBIT synergistic activity with combinations of several natural ingredients used in cosmetic skin care applications or house hold products that are known to have specific function such as topical therapeutic effect, antioxidant, skin conditioning, etc. and may or may not have antimicrobial activities.

The present invention is directed to a microbicidal composition comprising: (a) N-methyl-1,2-benzisothiazolin-3-one; and (b) at least one natural organic acid.

The invention is also directed to a method of inhibiting the growth of or controlling the growth of microorganisms comprising the step of adding the microbicidal composition to a household products; cosmetics; toiletries; shampoos; soaps; detergents; industrial cleaners; floor polishes; laundry rinse water; leather and leather products; textiles; textile products; agriculture adjuvant preservation; surfactant preservation; medical devices; diagnostic reagent preservation; toilet bowls; recreational water; pools; and spas.

Additionally, according to the present invention there is provided a coating composition comprising: (a) N-methyl-1,2-benzisothiazolin-3-one; and (b) at least one natural organic acid wherein the weight ratio of N-methyl-1,2-benzisothiazolin-3-one to natural organic acid may be from 1:10 to 1:33,333.

As used herein, the following terms have the designated definitions, unless the context clearly indicates otherwise. "MBIT" is N-methyl-1,2-benzisothiazolin-3-one.

The term "natural organic acid" synonymous with "organic acid" refers to azelaic acid (CAS No. 123-99-9), lactic acid (CAS No. 50-21-5), ferulic acid (CAS No. 1135-24-6), and undecylenic acid (CAS No. 112-38-9), preferably azelaic acid (CAS No. 123-99-9), lactic acid (CAS No. 50-21-5), and undecylenic acid (CAS No. 112-38-9).

The term "microbicide" synonymous with "antimicrobial" refers to a compound capable of killing, inhibiting the growth of or controlling the growth of microorganisms at a locus; microbicides include bactericides, fungicides and algaecides.

The term "microorganism" includes, for example, fungi (such as yeast and mold), bacteria, and algae, preferably fungi and bacteria.

The term "locus" refers to an industrial system or product subject to contamination by microorganisms. The following abbreviations are used throughout the specification: ppm=parts per million by weight (weight/weight), mL=milliliter, ATCC=American Type Culture Collection, MBC=minimum biocidal concentration, and MIC=minimum inhibitory concentration. Unless otherwise specified, temperatures are in degrees centigrade (° C.), and references to percentages (%) are by weight. Amounts of organic microbicides are given on an active ingredient basis in ppm (w/w).

The compositions of the present invention unexpectedly have been found to provide enhanced microbicidal efficacy at a combined active ingredient level lower than that of the individual microbicides. Additional microbicides beyond those listed in the claims may be present in the composition.

The antimicrobial composition comprises N-methyl-1,2-benzisothiazolin-3-one and an organic acid.

In some compositions of the present invention, the antimicrobial composition comprises N-methyl-1,2-benzisothiazolin-3-one and azelaic acid. Preferably, a weight ratio of N-methyl-1,2-benzisothiazolin-3-one to azelaic acid is from 1:50 to 1:105.

In some compositions of the present invention, the antimicrobial composition comprises N-methyl-1,2-benzisothiazolin-3-one and lactic acid. Preferably, a weight ratio of N-methyl-1,2-benzisothiazolin-3-one to lactic acid is from 1:125 to 1:33,333.

In some compositions of the present invention, the antimicrobial composition comprises N-methyl-1,2-benzisothiazolin-3-one and undecylenic acid. Preferably, a weight ratio of N-methyl-1,2-benzisothiazolin-3-one to undecylenic acid is from 1:10 to 1:212.

The microbicides in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycerin, glycol ethers, such as propylene glycol ether, diethyleneglycol monobutyl ether, dipropymyne glycol methyl ether, ethylene glycol ethylether, ethylene glycol monobutyl ether; alcohols, such as methanol, ethanol, propanol, isopropanol, phenethyl alcohol, phenoxyethanol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; oil such as mineral oil and plant oil such as wintergreen oil, castor oil, pine oil, almond oil, kernel oil and mixtures thereof. It is preferred that the solvent is selected from water, glycols, glycol ethers, esters and mixtures thereof. Suitable solid carriers include, for example, cyclodextrin, silicas, clay, animal fat, diatomaceous earth, waxes, cellulosic materials, alkali and alkaline earth (e.g., sodium, magnesium, potassium) metal salts (e.g., chloride, nitrate, bromide, sulfate) and charcoal.

When a microbicide component is formulated in a solvent, the formulation may optionally contain surfactants. When such formulations contain surfactants, they are generally in the form of emulsifiable concentrates, emulsions, microemulsive concentrates, or microemulsions. Emulsifiable concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

A microbicide component also can be formulated in the form of a dispersion. The solvent component of the dispersion can be an organic solvent or water, preferably water. Such dispersions can contain adjuvants, for example, co-solvents, chelants or sequestrans thickeners, anti-freeze agents, dispersants, fillers, pigments, surfactants, biodispersants, sulfosuccinates, terpenes, furanones, polycations, stabilizers, scale inhibitors and anti-corrosion additives.

Those skilled in the art will recognize that the microbicide components of the present invention may be added to a locus sequentially, simultaneously, or may be combined before being added to the locus. It is preferred that the first microbicide and the second microbicide component be added to a locus simultaneously or sequentially. When the microbicides are added simultaneously or sequentially, each individual component may contain adjuvants, such as, for example, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The microbicidal compositions of the present invention can be used to inhibit the growth of microorganisms) by introducing a microbicidally effective amount of the compositions onto, into, or at a locus subject to microbial attack. Suitable loci include, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners and sanitary wipes; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, wallboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

Preferably the microbicidal compositions of the present invention are used to inhibit the growth of microorganisms at a locus selected from household products; cosmetics; toiletries; shampoos; soaps; detergents; industrial cleaners; floor polishes; laundry rinse water; leather and leather products; textiles; textile products; agriculture adjuvant preservation; surfactant preservation; medical devices; diagnostic reagent preservation; toilet bowls; recreational water; pools; and spas.

The specific amount of the composition of this invention necessary to inhibit or control the growth of microorganisms and higher aquatic life forms in a locus depends upon the particular locus to be protected. Typically, the amount of the composition of the present invention to control the growth of microorganisms in a locus is sufficient if it provides from 0.1 to 1,000 ppm of the isothiazoline ingredient of the composition in the locus. It is preferred that the isothiazolone ingredients of the composition be present in the locus in an amount of at least 0.5 ppm, more preferably at least 4 ppm and most preferably at least 10 ppm. It is preferred that the isothiazolone ingredients of the composition be present in the locus in an amount of no more than 1000 ppm, more preferably no more than 500 ppm, and most preferably no more than 200 ppm.

The microbicidal compositions of the present invention may be included in a coating composition. N-methyl-1,2-benzisothiazolin-3-one and the at least one organic acid may be added to the coating composition separately or as a mixture or any combination thereof. Preferred coating compositions are liquid. Coating compositions may be aqueous or non-aqueous. Aqueous coating compositions generally contain 30% or more water by weight of the mixture, based on the weight of the coating composition.

Typically, the antimicrobial compositions are used to inhibit growth of algae, bacteria, and/or fungi, preferably bacteria, and/or fungi. It is contemplated that some embodiments may contain one or more additional antimicrobial compound.

EXAMPLES

Materials and Methods

The synergism of the combination of the present invention was demonstrated by testing a wide range of concentrations and ratios of the compounds.

One measure of synergism is the industrially accepted method described by Kull, F. C.; Eisman, P. C.; Sylwestrowicz, H. D. and Mayer, R. L., in *Applied Microbiology* 9:538-541 (1961), using the ratio determined by the formula:

$$Q_a/Q_A + Q_b/Q_B = \text{Synergy Index ("SI")}$$

wherein:

$Q_A$=concentration of compound A (first component) in ppm, acting alone, which produced an end point (MIC of Compound A).

$Q_a$=concentration of compound A in ppm, in the mixture, which produced an end point.

$Q_B$=concentration of compound B (second component) in ppm, acting alone, which produced an end point (MIC of Compound B).

$Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of a microbicide is the lowest concentration tested under a specific set of conditions that prevents the growth of added microorganisms. The microorganisms tested were *Escherichia coli* (*E. coli*, ATCC #8739), a yeast, *Candida albicans* (*C. albicans*, ATCC #10231) and mold, *Aspergillus niger* (*A. niger*, ATCC #16404).

MBIT synergy with a secondary biocide was determined by evaluating the minimum biocide or biocide blend concentration required to inhibit microbial growth. All studies were conducted using a 96 well microtiter plate format. For all studies, 200 μl of microbial growth media, containing various concentrations of MBIT alone, the secondary biocide alone, or combinations of both biocide chemistries, was added to individual wells of a microtiter plate. Specifically, Tryptic Soy Broth (TSB) was utilized for bacteria (*E. coli*, ATCC #8739), Yeast Malt Extract Broth (YMB) for yeast (*Candida albicans*, ATCC #10231) and Potato Dextrose Broth (PDB) for mold (*Aspergillus niger*, ATCC #16404). Test organisms, at a final concentration of $10^4$ CFU/mL or $10^4$ spores/mL, were applied to each well in parallel experiments to initiate the MIC evaluations. Growth medium containing no biocide was utilized as a control in each experimental setup to confirm the growth viability of each organism. Eight concentrations (2-fold dilutions) of each individual biocide were evaluated in the microbial growth inhibition studies in addition to the 64 possible combinations of these biocide concentrations. Evaluation of the individual biocide concentrations is required to achieve an inhibitory concentration end point for synergy index calculation. Following organism addition the 96-well microtiter plates were incubated at 25° C. for 48 hours or until growth was observed in the control wells containing no biocide. Individual wells were scored as growth or no growth based on visual organism growth turbidity. The lowest single active biocide concentrations resulting in no organism growth, for both MBIT and the secondary biocide, were recorded for synergy index calculations in addition to the combined biocide concentrations which resulted in an inhibition of microbial growth.

These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the MBIT with various natural organic acids are shown below in Tables 1-4.

TABLE 1

| Active Weight ratio of MBIT | Minimum Inhibitory Concentration (ppm) | | |
|---|---|---|---|
| and Azelaic acid | MBIT | Azelaic acid | Synergy Index |
| *E. coli* | | | |
| MBIT alone | 12.50 | 0 | |
| Azelaic acid alone | 0.00 | 2,500 | |
| No Synergy at any ratio | | | |
| *C. albicans* | | | |
| MBIT alone | 1.50 | 0 | |
| Azelaic acid alone | 0.00 | 187.5 | |
| 1:52 | 0.75 | 46.875 | 0.75 |
| 1:104 | 0.38 | 93.75 | 0.75 |
| *A. niger* | | | |
| MBIT alone | 25.00 | 0 | |
| Azelaic acid alone | 0.00 | 200,000 | |
| No Synergy at any ratio | | | |

MBIT: Azelaic acid showed synergy effect at ratio 1:50 to 1:105

TABLE 2

| Active Weight ratio of MBIT | Minimum Inhibitory Concentration (ppm) | | |
|---|---|---|---|
| and Lactic acid | MBIT | Lactic acid | Synergy Index |
| *E. coli* | | | |
| MBIT alone | 12.50 | 0 | |
| Lactic acid alone | 0.00 | 5,000 | |
| No Synergy at any ratio | | | |
| *C. albicans* | | | |
| MBIT alone | 1.50 | 0 | |
| Lactic acid alone | 0.00 | 750 | |
| 1:250 | 0.75 | 187.5 | 0.75 |
| 1:125 | 0.75 | 93.75 | 0.63 |
| *A. niger* | | | |
| MBIT alone | 25.00 | 0 | |
| Lactic acid alone | 0.00 | 40,000 | |
| 1:33,333 | 0.6 | 20000 | 0.74 |

MBIT: Lactic acid showed synergy effect at ratios 1:125 to 1:33,333

TABLE 3

| Active Weight ratio of MBIT | Minimum Inhibitory Concentration (ppm) | | |
|---|---|---|---|
| and Undecylenic acid | MBIT | Undecylenic acid | Synergy Index |
| *E. coli* | | | |
| MBIT alone | 12.50 | 0 | |
| Undecylenic acid | 0.00 | 10,000 | |
| No Synergy at any ratio | | | |
| *C. albicans* | | | |
| MBIT alone | 1.50 | 0 | |
| Undecylenic acid | 0.00 | 7.8175 | |
| 1:10 | 0.38 | 3.90625 | 0.75 |
| *A. niger* | | | |
| MBIT alone | 2.50 | 0 | |
| Undecylenic acid | 0.00 | 38 | |
| 1:30 | 0.63 | 19 | 0.75 |
| 1:61 | 0.31 | 19 | 0.63 |
| 1:212 | 0.16 | 19 | 0.56 |

MBIT: Undecylenic acid showed synergistic effect at ratios 1:10 to 1:212

The invention claimed is:

1. A synergistic microbicidal composition effective against mold and yeast comprising:
   (a) N-methyl-1,2-benzisothiazolin-3-one; and
   (b) at least one natural organic acid
wherein the organic acid is selected from the group consisting of lactic acid, and undecylenic acid;
further wherein when the organic acid is lactic acid the ratio of N-methyl-1,2-benzisothiazolin-3-one to lactic acid is from 1:125 to 1:33,333; and
further wherein when the organic acid is undecylenic acid the ratio of N-methyl-1,2-benzisothiazolin-3-one to undecylenic acid is from 1:10 to 1:212.

2. A product comprising the microbicidal composition of claim 1.

3. A synergistic microbicidal composition effective against yeast comprising:
   (a) N-methyl-1,2-benzisothiazolin-3-one; and
   (b) at least one natural organic acid;
wherein the organic acid is azelaic acid;
further wherein the weight ratio of N-methyl-1,2-benzisothiazolin-3-one to azelaic acid is from 1:50 to 1:105.

* * * * *